US006968841B2

(12) United States Patent
Fini

(10) Patent No.: US 6,968,841 B2
(45) Date of Patent: Nov. 29, 2005

(54) HEAT AND MOISTURE EXCHANGER

(75) Inventor: Massimo Fini, Mirandola (IT)

(73) Assignee: Mallinckrodt Holdings B.V., Deventer (NL)

( * ) Notice: Subject to any disclaimer, the term of this patent is extended or adjusted under 35 U.S.C. 154(b) by 0 days.

(21) Appl. No.: 10/862,665

(22) Filed: Jun. 7, 2004

(65) Prior Publication Data

US 2004/0216739 A1 Nov. 4, 2004

Related U.S. Application Data

(63) Continuation of application No. 09/979,634, filed as application No. PCT/IB01/00506 on Mar. 28, 2001, now Pat. No. 6,745,766.

(51) Int. Cl.[7] .................. A61M 16/00; F16K 11/00; G05D 11/02
(52) U.S. Cl. .................. 128/204.17; 128/201.13; 128/207.11
(58) Field of Search ............. 128/200.24, 200.26, 128/201.13, 201.25, 201.26, 203.26, 204.13, 128/204.15, 204.16, 204.17, 205.12, 205.17, 128/205.27, 205.29, 207.11, 207.14, 207.15, 128/207.16

(56) References Cited

U.S. PATENT DOCUMENTS

| | | | | |
|---|---|---|---|---|
| 3,326,214 A | * | 6/1967 | McCoy .................. | 128/201.13 |
| 3,747,598 A | * | 7/1973 | Cowans ................. | 128/201.13 |
| 3,881,482 A | * | 5/1975 | Lindholm .............. | 128/201.13 |
| 4,200,094 A | * | 4/1980 | Gedeon et al. ........ | 128/201.13 |
| 4,201,206 A | * | 5/1980 | Kuehn et al. .......... | 128/201.13 |
| 4,318,398 A | * | 3/1982 | Oetjen et al. .......... | 128/201.13 |
| 4,325,366 A | * | 4/1982 | Tabor ..................... | 128/207.16 |
| 4,458,679 A | * | 7/1984 | Ward ..................... | 128/201.13 |
| 4,771,770 A | * | 9/1988 | Artemenko et al. ... | 128/201.13 |
| 4,825,863 A | * | 5/1989 | Dittmar et al. ......... | 128/203.27 |
| 4,971,054 A | * | 11/1990 | Andersson et al. .... | 128/207.16 |
| 5,022,394 A | * | 6/1991 | Chmielinski ........... | 128/207.14 |
| 5,035,236 A | * | 7/1991 | Kanegaonkar ......... | 128/201.13 |
| 5,038,792 A | * | 8/1991 | Mault .................... | 600/531 |
| 5,042,468 A | * | 8/1991 | Lambert ................ | 128/200.26 |
| 5,131,387 A | * | 7/1992 | French et al. .......... | 128/205.27 |
| 5,195,527 A | * | 3/1993 | Hicks ..................... | 128/205.12 |
| 5,259,378 A | * | 11/1993 | Huchon et al. ........ | 128/207.16 |
| 5,320,096 A | * | 6/1994 | Hans ...................... | 128/205.29 |
| 5,383,447 A | * | 1/1995 | Lang ...................... | 128/201.13 |
| 5,386,825 A | * | 2/1995 | Bates ..................... | 128/205.27 |
| 5,438,978 A | * | 8/1995 | Hardester, III ......... | 128/201.13 |
| 5,460,172 A | * | 10/1995 | Eckerbom et al. ..... | 128/201.13 |
| 5,577,494 A | * | 11/1996 | Kuypers et al. ........ | 128/201.13 |
| 5,590,644 A | * | 1/1997 | Rosenkoetter ......... | 128/201.13 |
| 5,592,933 A | * | 1/1997 | Zucchi ................... | 128/201.13 |
| 5,616,158 A | * | 4/1997 | Biendarra et al. ...... | 96/117.5 |
| 5,617,913 A | * | 4/1997 | DeGregoria et al. ... | 165/104.11 |
| 5,647,344 A | * | 7/1997 | Turnbull ................ | 128/201.13 |
| 5,662,161 A | * | 9/1997 | Hughes et al. ......... | 165/10 |
| 5,666,950 A | * | 9/1997 | Smith ..................... | 128/207.14 |
| 5,701,891 A | * | 12/1997 | Groenke ................ | 128/205.29 |

(Continued)

FOREIGN PATENT DOCUMENTS

WO   WO99/60954   12/1999

*Primary Examiner*—Henry Bennett
*Assistant Examiner*—Nihir Patel
(74) *Attorney, Agent, or Firm*—Baker Botts L.L.P.

(57) ABSTRACT

A device for passive humidification of tracheostomized or intubated patients, comprising an outer body which forms an opening for connection to the patient and is connected to at least one seat of a filtering element which is connected to the outside, the device further comprising, on the outer body, a coupling for connection to at least one oxygen delivery duct which ends proximate to the outer part of the filtering element.

6 Claims, 1 Drawing Sheet

U.S. PATENT DOCUMENTS

| | | | |
|---|---|---|---|
| 5,738,095 A * | 4/1998 | Persson | 128/207.14 |
| 5,829,428 A * | 11/1998 | Walters et al. | 128/200.24 |
| 5,848,590 A * | 12/1998 | Smith | 128/201.13 |
| 5,964,221 A * | 10/1999 | McKenna | 128/205.12 |
| 5,983,894 A * | 11/1999 | Fukunaga et al. | 128/205.29 |
| 5,992,413 A * | 11/1999 | Martin et al. | 128/201.13 |
| 6,010,118 A * | 1/2000 | Milewicz | 261/142 |
| 6,041,778 A * | 3/2000 | Swann et al. | 128/201.25 |
| 6,095,135 A * | 8/2000 | Clawson et al. | 128/201.13 |
| 6,105,576 A * | 8/2000 | Clawson et al. | 128/205.12 |
| 6,116,235 A * | 9/2000 | Walters et al. | 128/200.24 |
| 6,123,076 A * | 9/2000 | Roberts et al. | 128/205.29 |
| 6,330,883 B1 * | 12/2001 | Berger | 128/201.13 |
| 6,363,930 B1 * | 4/2002 | Clawson et al. | 128/201.13 |
| 6,415,788 B1 * | 7/2002 | Clawson et al. | 128/201.13 |
| 6,422,235 B1 * | 7/2002 | Persson | 128/200.26 |
| 6,550,476 B1 * | 4/2003 | Ryder | 128/201.13 |
| 6,554,261 B2 * | 4/2003 | Katagiri et al. | 261/154 |
| 6,745,766 B2 * | 6/2004 | Fini | 128/204.17 |
| 6,755,399 B2 * | 6/2004 | Shimanuki et al. | 261/104 |
| 6,769,430 B1 * | 8/2004 | Carlsen et al. | 128/201.13 |
| 6,792,946 B1 * | 9/2004 | Waldo et al. | 128/205.12 |

* cited by examiner

HEAT AND MOISTURE EXCHANGER

RELATED APPLICATIONS

This is a continuation of Ser. No. 09/979,634 filed Nov. 26, 2001, now U.S. Pat. No. 6,745,766, which is a national phase of PCT/IB01/00506, filed 28 Mar. 2001, claiming priority from Italian application MI2000A000659, filed 29 Mar. 2000.

TECHNICAL FIELD

The present invention relates to a device for passive humidification of tracheostomized or intubated patients.

BACKGROUND ART

Currently, in patients with tracheal intubation and tracheostomized patients devices are used for compensating for the lack of humidification and heating of the inspired gases which occurs in normal conditions in the upper respiratory tract.

In order to perform this function, these devices are constituted by a hygroscopic element, generally constituted by a coiled ribbon which is meant to retain moisture and heat during expiration and release them during inspiration.

Currently known embodiments are generally relatively bulky and therefore they are poorly accepted in home-care cases; moreover, they require the presence of additional devices whenever it is necessary to perform oxygen enrichment.

Another problem is that if bronchoaspiration is to be performed, the device must be removed from the patient, with the obvious related difficulties.

DISCLOSURE OF THE INVENTION

The aim of the present invention is to eliminate the above noted drawbacks, by providing a device for passive humidification of tracheostomized or intubated patients which is designed so as to be particularly suitable for home care since it has a flattened shape which is aesthetically more acceptable, thus facilitating the social impact of the discharged patient.

Within this aim, a particular object of the invention is to provide a device in which it is possible to perform oxygen enrichment without having to resort to external devices and which also allows to perform bronchoaspiration without removing the device from the patient.

Another object of the present invention is to provide a device which by virtue of its particular constructive characteristics is capable of giving the greatest assurances of reliability and safety in use.

Another object of the present invention is to provide a device for passive humidification of tracheostomized or intubated patients which can be easily obtained starting from commonly commercially available elements and materials and is also competitive from a merely economical point of view.

This aim and these and other objects which will become better apparent hereinafter are achieved by a device for passive humidification of tracheostomized or intubated patients, according to the invention, comprising an outer body which has an opening for connection to the patient and is connected to at least one seat of a filtering element which is connected to the outside, characterized in that it comprises, on said outer body, a coupling for connection to at least one oxygen delivery duct which ends proximate to the outer part of said filtering element.

BRIEF DESCRIPTION OF THE DRAWINGS

Further characteristics and advantages will become better apparent from the description of a preferred but not exclusive embodiment of a device for passive humidification of tracheostomized or intubated patients, illustrated only by way of non-limitative example in the accompanying drawings, wherein.

WAYS OF CARRYING OUT THE INVENTION

Figure 1:
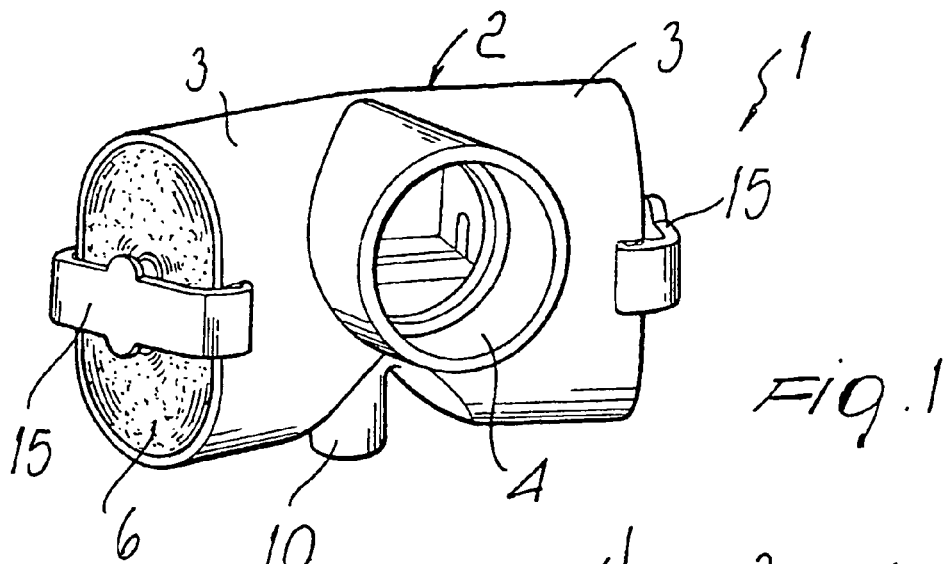
FIG. 1 is a perspective view of the device according to the invention, taken from the side directed toward the patient.
Figure 2:
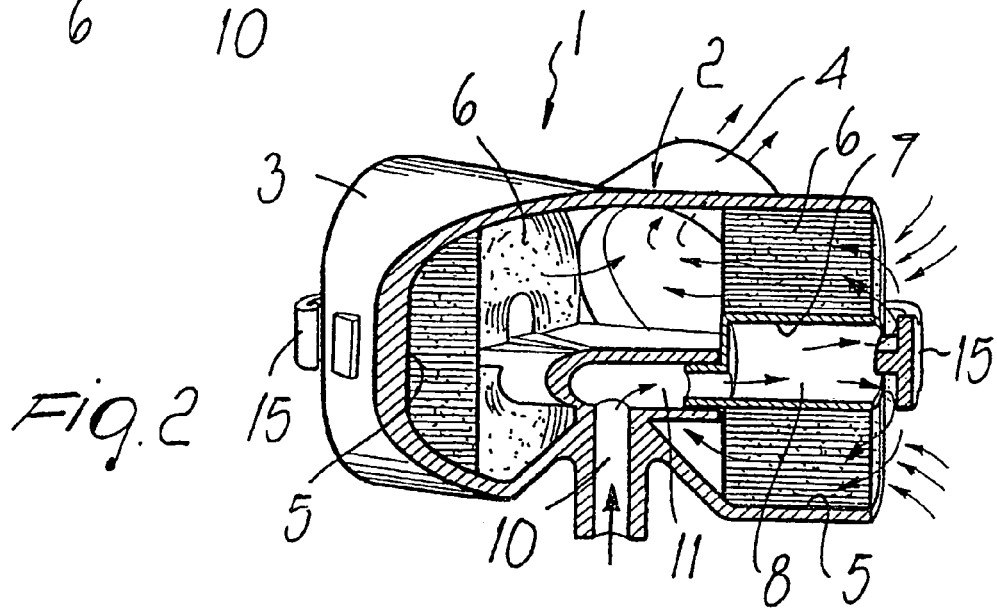
FIG. 2 is a partially cutout view of the device.
Figure 3:
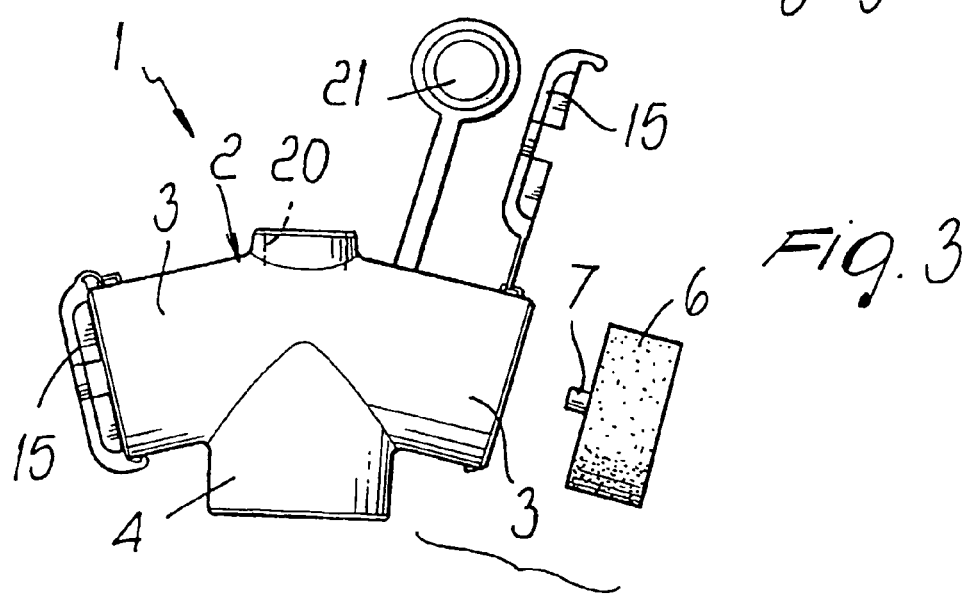
FIG. 3 is a plan view of the device.

With reference to the figures, the device for passive humidification of tracheostomized or intubated patients, according to the invention, generally designated by the reference numeral 1, comprises an outer body 2 which is formed by a pair of flattened and mutually inclined wings 3 between which there is an opening 4 for connection to the patient.

Two seats 5 are formed inside the outer body 2, specifically at the ends of the wings, and are arranged symmetrically with respect to the centerline of the outer body; respective filtering elements 6 can be accommodated in said seats and are constituted, in a per se known manner, by a ribbon optionally impregnated with hygroscopic salts, which is wound around a core 7 which internally forms a channel 8 which is connected to a coupling 10 which is in turn connected to an oxygen delivery duct 11 which divides into two branches so as to connect both channels 8, which end at the outer face of the filtering element 6.

In the region where the channel 8 ends, there is a cross-member 15 which is adapted to retain the filtering element in its seat and further forms a redirection element which, being spaced from the output end of the channel 8, conveys the oxygen back onto the outer surface of the filtering element, thus achieving air enrichment.

The outer body 2 has, at the opposite end with respect to the opening 4 for connection to the patient, a port 20 which can be closed by a plug 21 and which, by being in practice axially aligned with the opening 4, allows to perform bronchoaspiration without having to remove the device from the patient.

From the above description it is thus evident that the invention achieves the intended aim and objects, and in particular the fact is stressed that a device for passive humidification of tracheostomized or intubated patients is provided which in addition to having an aesthetically pleasant shape is extremely practical and functional, since it directly integrates the channels for performing oxygen enrichment.

Moreover, the presence of the port 20 allows to perform bronchoaspiration without removing the device from the patient.

The invention thus conceived is susceptible of numerous modifications and variations, all of which are within the scope of the inventive concept.

All the details may further be replaced with other technically equivalent elements.

In practice, the materials used, as well as the contingent shapes and dimensions, may be any according to requirements.

The disclosures in Italian Patent Application No. MI2000A000659, from which this application claims priority, are incorporated herein by reference.

What is claimed is:

1. A device for passive humidification of tracheostomized or intubated patients, comprising:
   at least one filtering and humidifying element having an internal channel;
   an outer body enclosing said at least one filtering and humidifying element, said outer body having a first opening adapted to connect to a patient, at least one second opening adapted to receive said at least one filtering and humidifying element, at least one oxygen delivery duct, and a coupling on said outer body connected to said at least one oxygen delivery duct, said internal channel of said at least one filtering and humidifying element being connected to said at least one oxygen delivery duct to conduct oxygen from said, at least one oxygen delivery duct through said internal channel; and
   at least one cross-member having a first end pivotally connected to said outer body and a second end removably connected to said outer body for removably retaining said at least one filtering and humidifying element in said outer body, said at least one cross-member being spaced apart from said channel of said at least one filtering and humidifying element and redirecting oxygen from said channel through said at least one second opening of said outer body through said at least one filtering and humidifying element to said first opening, so as to filter and humidify said oxygen supplied to the patient from said oxygen delivery duct.

2. The device according to claim 1, wherein said at least one filtering and humidifying element comprises two filtering and humidifying elements, said at least one second opening comprises two second openings, and said outer body comprises two mutually inclined flattened wings including said two second openings for receiving said filtering humidifying elements.

3. The device according to claim 2, wherein said first opening is arranged between said wings.

4. The device according to claim 1, wherein said at least one filtering and humidifying element comprises a ribbon which is wound on a core which internally forms said internal channel connected to said oxygen delivery duct.

5. The device according to claim 1, wherein said at least one delivery duct comprises a plurality of branches, and said coupling is connected to said plurality of branches of said at least one delivery duct, and wherein said plurality of branches are arranged mutually opposite.

6. The device according to claim 1, wherein said outer body comprises a port which can be removably closed by a plug, and wherein said port is arranged so as to be substantially axially aligned with respect to said first opening.

* * * * *